(12) United States Patent
MacDonald et al.

(10) Patent No.: US 8,466,153 B2
(45) Date of Patent: Jun. 18, 2013

(54) PIPERIDINYLAMINO-PYRIDAZINES AND THEIR USE AS FAST DISSOCIATING DOPAMINE 2 RECEPTOR ANTAGONISTS

(75) Inventors: Gregor James MacDonald, Zoersel (BE); José Ignacio Andrés-Gil, Madrid (ES); Frans Alfons Maria Van Den Keybus, Essen (BE); José Manuel Bartolomé-Nebreda, Toleda (ES); Michiel Luc Maria Van Gool, Madrid (ES)

(73) Assignee: Janssen Pharmaceutica N.V., Beerse (BE)

( * ) Notice: Subject to any disclaimer, the term of this patent is extended or adjusted under 35 U.S.C. 154(b) by 504 days.

(21) Appl. No.: 12/516,645

(22) PCT Filed: Dec. 5, 2007

(86) PCT No.: PCT/EP2007/063338
§ 371 (c)(1),
(2), (4) Date: May 28, 2009

(87) PCT Pub. No.: WO2008/068277
PCT Pub. Date: Jun. 12, 2008

(65) Prior Publication Data
US 2010/0076187 A1    Mar. 25, 2010

(30) Foreign Application Priority Data

Dec. 8, 2006   (EP) .................................. 06125685

(51) Int. Cl.
*A61K 31/501*   (2006.01)
*C07D 237/20*   (2006.01)
*A61P 25/28*    (2006.01)

(52) U.S. Cl.
USPC ..................................... 514/252.06; 544/238

(58) Field of Classification Search
USPC ..................................... 544/238; 514/252.06
See application file for complete search history.

(56) References Cited

U.S. PATENT DOCUMENTS

| | | | |
|---|---|---|---|
| 3,933,832 A | 1/1976 | Langbein et al. | |
| 4,126,689 A | 11/1978 | Sanczuk et al. | |
| 4,197,304 A | 4/1980 | Sanczuk et al. | |
| 4,585,471 A | 4/1986 | Forster et al. | |
| 5,736,545 A | 4/1998 | Gadwood et al. | |
| 5,866,589 A | 2/1999 | Romero et al. | |
| 7,754,774 B2 | 7/2010 | Kobayashi et al. | |
| 8,058,243 B2 | 11/2011 | Tyers et al. | |
| 2008/0227791 A1 | 9/2008 | Bruyn et al. | |
| 2011/0130408 A1 | 6/2011 | Bartolme-Nebreda et al. | |

FOREIGN PATENT DOCUMENTS

| | | |
|---|---|---|
| DE | 2642856 C2 | 9/1976 |
| DE | 3218482 A1 | 5/1982 |
| EP | 281309 B1 | 9/1988 |
| EP | 0532178 B1 | 3/1993 |
| EP | 1443046 B1 | 4/2001 |
| EP | 1506185 B1 | 2/2005 |
| EP | 1621538 B1 | 2/2006 |
| WO | WO 96/18628 A1 | 6/1996 |
| WO | WO 96/35666 A1 | 11/1996 |
| WO | WO 99/09025 A1 | 2/1999 |
| WO | WO 99/36407 A1 | 7/1999 |
| WO | WO 01/98273 A1 | 12/2001 |
| WO | WO 02/068409 A1 | 9/2002 |
| WO | WO 03/049736 A1 | 6/2003 |
| WO | WO 03/062215 A1 | 7/2003 |
| WO | WO 03/066604 A2 | 8/2003 |
| WO | WO 03/0725548 A1 | 9/2003 |
| WO | WO 2005/005779 A2 | 1/2005 |
| WO | 2005/009976 | 2/2005 |
| WO | WO 2005/013907 A2 | 2/2005 |
| WO | WO 2005/105779 A1 | 11/2005 |
| WO | WO 2005/117883 A1 | 12/2005 |
| WO | WO 2006/034440 A2 | 3/2006 |
| WO | WO 2006/055187 A1 | 5/2006 |
| WO | WO 2007/001975 A1 | 1/2007 |
| WO | WO 2007/048779 A1 | 5/2007 |
| WO | WO 2007/130383 A2 | 11/2007 |
| WO | WO 2008/019967 A2 | 2/2008 |
| WO | WO 2008/098892 A1 | 8/2008 |
| WO | WO 2010/012758 A1 | 2/2010 |

OTHER PUBLICATIONS

Contreras, J-M, et al. "Aminopyridazines as Acetylcholinesterase Inhibitors", J. Med. Chemistry (1999) vol. 42, pp. 730-741.
Goodman, A., et al. "Desymmetrization of Dichlorazaheterocycles", Tetrahedron 55 (1999) pp. 15067-15070.
Kapur, S., et al. "Does Fast Dissociation From the Dopamine $D_2$ Receptor Explain the Action of Atypical Antipsychotics?: A New Hypothesis", Am. J. Psychiatry (Mar. 2001) vol. 158:3, pp. 360-369 (XP-002432148).
Leysen, J., et al. "The Dissociation Rate of Unlabelled Dopamine Antagonists and Agonists From the Dopamine-$D_2$ Receptor, Application of an Original Filter Method", Journal of Receptor Research (1984) vol. 4(7), pp. 817-845.

(Continued)

*Primary Examiner* — Susanna Moore
(74) *Attorney, Agent, or Firm* — Peter Herridge

(57) ABSTRACT

The present invention relates to 6-(piperidin-4-ylamino)pyridazin-3-carbonitriles of the general formula (I);

(I)

or a pharmaceutically acceptable salt thereof, or a stereoisomeric form, that are fast dissociating dopamine 2 receptor antagonists, as well as processes for preparing these compounds, pharmaceutical compositions comprising these compounds as an active ingredient. The compounds find utility as medicines for treating or preventing central nervous system disorders, for example schizophrenia, by exerting an antipsychotic effect without motor side effects.

7 Claims, No Drawings

OTHER PUBLICATIONS

Moragues, J., et al. "Dopaminergic Activity in a Series of N-Substituted 2-Aminopyrimidines", Farmaco, Edizinone Scientifica (1980) vol. 35, No. 11, pp. 951-964(XP-009032424).
Abbott, A., "The Molecular Wake-Up Call", Nature, vol. 447, pp. 368-370 (2007).
Arlt, M., et. al., "SAR of Novel Biarylmethylamine Dopamine $D_4$ Receptor Ligands", Bioorganic & Medicinal Chemistry Letters, vol. 8, pp. 2033-2038 (1998).
Bartoszyk, Gerd D., "Anxiolytic Effects of Dopamine Receptor Ligands" 1. Involvement of Dopamine Autoreceptors, life Sciences, vol. 62, No. 7, pp. 649-653 (1998).
Benjamin, E., et al., "Pharmacological Characterization of Recombinant N-type Calcium Channel ($Ca_v2/2$) Mediated Calcium Mobilization Using FLIPR", Biochemical Pharmacology, vol. 72, pp. 770-782 (2006).
Bianchi, Z., "Current Issues in Central Nervous System Drug Development", (2012).
Binggeli, A., et al., "Phenyl, Pyridine and Quinoline Derivatives as SST5 Receptor Modulators and Their Preparation, Pharmaceutical Compositon and Use in the Treatment of Disease", CAPLUS: 2008:222500 (2008).
Braga, D., et al. "Making Crystals from Crystals: A Green Route to Crystal Engineering and Polymorphism", Chemical Communications, pp. 3653-3645 (2005).
Cell Surface Receptor, Wikipedia Feb. 2, 2012.
Chabner, B., et al., "Antineoplastic Agents", Goodman & Gilmans the Pharmacological Basis of Therapeutics, Section IX, Chapter 51, pp. 1315-1403 (2006).
Contreras, J-M, et al. "Aminopyridazines as Acetylcholinesterase Inhibitors", J. Medicinal Chemistry, vol. 42, pp. 730-741 (1999).
Cook, A., et al. "Preparation of 2-Aminopyridine Derivatives as Nitric Oxide Synthase Inhibitors", Caplus 2000:335406 (2000).
Dean, W., et al. "Condensation of Arylacetonitriles With Glyoxylic Acid. Facile Synthesis of Arylmaleic Acid Derivatives", Journal of Organic Chemistry, vol. 58, pp. 7916-7917 (1993).
Eichenberger, von K., et al., "Heilmittelchemische Studien in der Heterocyclischen Reihe" Volumen XXXIX, No. 208 (1956) (Non English).
Fryatt, T., et al., "Novel Quinolinequinone Antitumor Agents; Structure-Metabolism Studies with NAD(P)H:quinine Oxidoreductase (NQO1)", Bioorganic & Medicinal Chemistry, vol. 12, pp. 1667-1687 (2004).
Genin, M., et al. "Synthesis and Structure-Activity Relationships of the (Alkylamino)Piperidine-Containing BHAP Class of Non-Nucleoside Reverse Transcriptase Inhibitors: Effect of 3-Alkylpryidine Ring Substitution", Journal of Medicinal Chemistry, vol. 42, pp. 4140-4149 (1999).
Genin, M., et al., "Synthesis and Bioactivity of Novel Bis(heteroaryl)piperazine (BHAP) Reverse Transcriptase Inhibitors: Structure-Activity Relationships and Increased Metabolic Stability of Novel Substituted Pyridine Analogs", J. Med. Chemistry, vol. 39, pp. 5267-5725 (1996).
Gillaspy, M., et al. "A Simple Method for the Formation of Cyclopropylamines: The First Synthesis of Tricyclopropylamine", Tetrahedron Letters, vol. 36, No. 41, pp. 7399-7402 (1995).
Goodman, A., et al. "Desymmetrization of Dichloroazaheterocycles", Tetrahedron, vol. 55, pp. 15067-15070 (1999).
Griesser, Ulrich, "The Importance of Solvates", Polymorphism: In the PharmaceuticalIndsutry, pp. 211-234 (2006).
Grundt, P., et al., "Analogues of the Dopamine D2 Receptor Antagonist L741, 626: Binding, Function and SAR", Bioorganic Med. Chem. Lett. vol. 17(3), pp. 745-749 (2007).
Holenz, J., et al. Medicinal Chemistry Strategies to 5-$HT_6$ Receptor Ligands as Potential Cognitive Enhances and Antiobesity Agents, Drug Discovery Today, vol. 11, No. 7/8, pp. 283-299 (2006).
Joyce, J., et al., "Dopamine $D_3$ Receptor Antagonists as Therapeutic Agents", Drug Discovery Today, vol. 10, No. 18, pp. 917-925 (2005).
Kapitulnik, Jaime, "Drug Transport and Metabolism in the Blood-Brain Barrier", Frontiers in Pharmacology, vol. 2, (2011).

Kapur, S., et al. "Does Fast Dissociation From the Dopamine $D_2$ Receptor Explain the Action of Atypical Antipsychotics?: A New Hypothesis", Am. J. Psychiatry, vol. 158, pp. 360-369 (2001).
Kikuchi, C., et al. "Tetrahydrobenzindoles: Selective Antagonists of the 5-$HT_7$ Receptor", Journal of Medicinal Chemistry, vol. 42, No. 4, pp. 533-535. (1999).
Kortagere, S., et al., "Certain 1,4-Disubstituted Aromatic Piperidines and Piperazines with Extreme Selectivity for the Dopamine D4 Receptor Interact with a Common Receptor Microdomain", Molecular pharmacology, vol. 66, No. 6, pp. 1491—(2004).
Kula, N., et al. Neuropharmacological Assessment of Potential Dopamine $D_4$ . Receptor-Selective Radioligands, European Journal of Pharmacology, vol. 367, pp. 139-142 (1999).
Kula, N., et al. "RBI-257: A Highly Potent Dopamine $D_4$ Receptor-Selective Ligand", European Journal of Pharmacology, vol. 331, pp. 333-336 (1997).
Kula, N., et al. "RBII-257: A Highly Potent Dopamine D4 Receptor-Selective Ligand", Caplus 1997:453167 (1997).
Leysen, J., et al. The Dissociation Rate of Unlabelled Dopamine Antagonists and Agonists From the Dopamine-$D_2$ Receptor, application of an Original Filter Method, Journal of Receptor Research, vol. 4(7), pp. 817-845 (1984).
Lovenberg, T., et al., "Cloning of Rat Histamine $H_3$ Receptor Reveals Distinct Species Pharmacological Profiles", The Journal of Pharmacology and Experimental Therapeutics, vol. 293, No. 3, pp. 771—(2000).
Mitchell, E., et al. "5-$HT_6$ Receptors: A Novel Target for Cognitive Enhancement", Pharmacology & Therapeutics, vol. 108, pp. 320-333 (2005).
Moragues, J., et al., "Dopaminergic Activity in a Series of N-Substituted 2-Aminopyrimidines", II Farmaco, Ed. Sc.. vol. 35, pp. 951-964 XP009032424 (1980).
Munson, P., et al., "Synthesis of 2-Alkylamino-3-Fluoropyridines Using Buchwald Conditions", Synthetic Communications, vol. 34, No. 5, pp. 759-766 (2004).
Okuyama, S., et al. A Selective Dopamine $D_4$ Receptor Antagonists, NRA0160: A Preclinical Neuropharmacological Profile, Life Sciences, vol. 65, No. 20, pp. 2109-2125 (1999).
Phedias, D., et al. "Compositions and Methods for Treating Neurological Disorders or Damage", Caplus 2008:493012 (2008).
Poupaert, J., "Drug Design: Basic Principles and Applications", Encyclopedia of Pharmaceutical Technology, pp. 1362 (2007).
Rodefer, J., et al. "Reversal of Subchronic PCP-Induced Deficits in Attentional Set Shifting in Rats by Sertindole and a 5-$HT_6$ Receptor Antagonist: Comparison Among Antipsychotics", Neuropsychopharmacology, vol. 33, pp. 2657-2666 (2008).
Schlachter, S., et a. "Substituted 4-Aminopiperidines Having High in vitro Affinity and Selectivity for the Cloned Human Dopamine $D_4$ Receptor" European Journal of Pharmacology, vol. 322, pp. 283-286 (1997).
Seddon, Kenneth, "Pseudopolymorph: A Polemic", Perspective, Crystal Growth & Design, vol. 4, No. 6, (2004).
Tao, B., et al. "Trans-Pd(OAC)$_2$NH)$_2$ Catalyzed Suzuki Coupling Reactions and Its Temperature-Depednent Activities Toward Aryl Bromides", Tetrahedron Letters, vol. 44, pp. 7993-7996 (2003).
Ten Brink, R., et al., "Preparation of Heterocyclic Compounds for the Treatment of Cns and Cardiovascular Disorders", Caplus: 1995: 951193 (1995).
Vippagunta, S., et al. "Crystalline Solids", Advanced Drug Discovery Reviews, vol. 48, pp. 3-26 (2001).
Wood, M., et al., Aripiprazole Acts as a Selective Dopamine $D_2$ Receptor Partial Agonist, Perspective, Expert Opinion on Investigative Drugs, vol. 16(6), pp. 771-775 (2007).
Xiao, D., et al., "Discovery of a Series of Potent Arylthiadiazole $H_3$ Antagonists", Bioorganic & Medicinal Chemistry Letters, vol. 21, pp. 861-864 (2011).

Yamada, K., eta I. "Involvement of Septal and Striatral Dopamine D-2 Receptors in Yawning Behavior in Rats", Psychopharmacology, vol. 90, pp. 9-13 (1986).

Zablotskaya, a., et al. "Silyl Modification of Biologically Active Compunds.8*. Trimethylsilyl Ethers of Hydroxyl-Containing Thiazole Derivatives", Chemistry of Heterocyclic Compounds, vol. 38, No. 7, pp. 859 (2002).

Zhang, a., et al. "Recent Advances Towards the Discovery of Dopamine Receptor Ligands", Expert Opinion on Therapeutic Patents vol. 16(5), pp. 587-630 (2006).

International Search Report for corresponding application No. PCT/EP2006/067696 mailed Mar. 13, 2007.

International Search Report for corresponding application No. PCT/EP2008/051597 mailed Jun. 19, 2008.

International Search report for corresponding application No. PCT/EP2007/063338 mailed Dec. 2, 2008.

International Search report for corresponding application No. PCT/EP2008/054732 mailed Sep. 5, 2008.

International Search report for corresponding application No. PCT/EP2008/054730 mailed Jul. 9, 2007.

International Search report for corresponding application No. PCT/EP2009/059788 mailed Sep. 10, 2009.

International Search Report for corresponding application No. PCT/EP2009/004745 mailed Aug. 28, 2009.

International Search Report for corresponding application No. PCT/EP2008/054731 mailed Sep. 30, 2008.

Wikipedia, "Cell Surface Receptor", Wikipedia, Feb. 2, 2012 pp. 1-6.

PIPERIDINYLAMINO-PYRIDAZINES AND THEIR USE AS FAST DISSOCIATING DOPAMINE 2 RECEPTOR ANTAGONISTS

CROSS REFERENCE TO RELATED APPLICATIONS

This application is a national stage application of Patent Application No. PCT/EP2007/063338, filed Dec. 5, 2007, which in turn claims the benefit of EPO Patent Application No. 06125685.5 filed Dec. 8, 2006. The complete disclosures of the aforementioned related patent applications are hereby incorporated herein by reference for all purposes.

FIELD OF THE INVENTION

The present invention relates to 6-(piperidin-4-ylamino) pyridazin-3-carbonitriles that are fast dissociating dopamine 2 receptor antagonists, processes for preparing these compounds and pharmaceutical compositions comprising these compounds as an active ingredient. The compounds find utility as medicines for treating or preventing central nervous system disorders, for example schizophrenia, by exerting an antipsychotic effect without motor side effects.

BACKGROUND PRIOR ART

J. Med. Chem. (1999), 42 (4), 730-741 discloses 6-phenyl-N-[1-(phenylmethyl)-4-piperidinyl]-3-pyridazinamine and analogous compounds as acetylcholinesterase inhibitors.

Farmaco, Vol. 35, no. 11, 1980, pages 951-964 discloses substituted N-[4-piperidinyl]-2-aminopyrimidines having dopaminergic activity, i.e. most of the disclosed compounds are agonists at the dopamine D2 receptor. Since none of the compounds tested antagonized the stereotyped behavior induced by a subsequent dose of apomorphine they may also be considered to be devoid of dopamine receptor blocking properties. The compounds of the present invention differ in the presence of a pyridazine instead of a pyrimidine moiety and the unexpected finding that they exert an antagonistic effect at the dopamine D2 receptor.

DESCRIPTION OF THE INVENTION

Schizophrenia is a severe and chronic mental illness that affects approximately 1% of the population. Clinical symptoms are apparent relatively early in life, generally emerging during adolescence or early adulthood. The symptoms of schizophrenia are usually divided into those described as positive, including hallucinations, delusions and disorganised thoughts and those referred to as negative, which include social withdrawal, diminished affect, poverty of speech and the inability to experience pleasure. In addition, schizophrenic patients are suffering from cognitive deficits, such as impaired attention and memory. The aetiology of the disease is still unknown, but aberrant neurotransmitter actions have been hypothesized to underlie the symptoms of schizophrenia. The dopaminergic hypothesis is one most often considered; it proposes that hyperactivity of dopamine transmission is responsible for the positive symptoms observed in schizophrenic patients. This hypothesis is based on the observation that dopamine enhancing drugs, such as amphetamine or cocaine, may induce psychosis, and on the correlation that exists between clinical doses of antipsychotics and their potency in blocking dopamine D2 receptors. All marketed antipsychotics mediate their therapeutic efficacy against positive symptoms by blocking the dopamine D2 receptor. Apart from the clinical efficacy, it appears that the major side effects of antipsychotics, such as extrapyramidal symptoms (EPS) and tardive dyskinesia, are also related to dopamine antagonism. Those debilitating side effects appear most frequently with the typical or first generation of antipsychotic (e.g., haloperidol). They are less pronounced with the atypical or second generation of antipsychotic (e.g., risperidone, olanzapine) and even virtually absent with clozapine, which is considered the prototypical atypical antipsychotic. Among the different theories proposed for explaining the lower incidence of EPS observed with atypical antipsychotics, the one that has caught a lot of attention during the last fifteen years, is the multireceptor hypothesis. It follows from receptor binding studies showing that many atypical antipsychotics interact with various other neurotransmitter receptors in addition to dopamine D2 receptors, in particular with the serotonin 5-HT2 receptors, whereas typical antipsychotic like haloperidol bind more selectively to the D2 receptors. This theory has been challenged in recent years because all major atypical antipsychotics fully occupy the serotonin 5-HT2 receptors at clinically relevant dosages but still differ in inducing motor side-effects. As an alternative to the multireceptor hypothesis, Kapur and Seeman ("Does fast dissociation from the dopamine D2 receptor explain the action of atypical antipsychotics?: A new hypothesis", Am. J. Psychiatry 2001, 158:3 p. 360-369) have proposed that atypical antipsychotics can be distinguished from typical antipsychotics by the rates at which they dissociate from dopamine D2 receptors. The fast dissociation from the D2 receptor would make an antipsychotic more accommodating of physiological dopamine transmission, permitting an antipsychotic effect without motor side effects. This hypothesis is particularly convincing when one considers clozapine and quetiapine. These two drugs have the fastest rate of dissociation from dopamine D2 receptors and they carry the lowest risk of inducing EPS in humans. Conversely, typical antipsychotics associated with a high prevalence of EPS, are the slowest dissociating dopamine D2 receptor antagonists. Therefore, identifying new drugs based on their rate of dissociation from the D2 receptor appears as a valid strategy to provide new atypical antipsychotics. An additional goal is to combine fast dissociating properties with selectivity for dopamine D2 receptors. The multiple receptor profile of current atypical antipsychotics is thought to be the cause of other side effects, such as weight gain and diabetes. Searching for selective D2 antagonists has been ignored as an approach for some time but it is our belief that using more selective compounds in clinic may reduce the occurrence of metabolic disorders associated with current atypical antipsychotic drugs.

It is the object of the present invention to provide novel compounds that are fast dissociating dopamine 2 receptor antagonists which have an advantageous pharmacological profile as explained before, in particular reduced motor side effects, and moderate or negligible interactions with other receptors resulting in reduced risk of developing metabolic disorders.

This goal is achieved by the present novel compounds according to Formula (I):

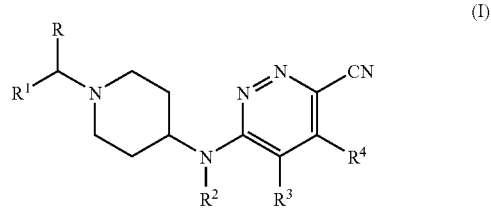

the pharmaceutically acceptable salts and solvates thereof, and stereoisomeric forms thereof, wherein R is hydrogen or $C_{1-6}$alkyl;

$R^1$ is phenyl; phenyl substituted with 1, 2 or 3 substituents each independently selected from the group consisting of hydrogen, halo, cyano, $C_{1-4}$alkyl, $C_{1-4}$alkyloxy, perfluoro$C_{1-4}$alkyl, and trifluoromethoxy; thienyl; thienyl substituted with 1 or 2 substituents selected from the group consisting of halo and $C_{1-4}$alkyl; $C_{1-4}$alkyl; $C_{1-4}$alkyl substituted with hydroxyl, $C_{3-8}$cycloalkyl or $C_{5-7}$cycloalkenyl; $C_{3-8}$cycloalkyl; or $C_{5-7}$cycloalkenyl;

$R^2$ is hydrogen or $C_{1-6}$alkyl;

$R^3$ and $R^4$ each independently are hydrogen, $C_{1-4}$alkyl or halo, or $R^3$ and $R^4$ together form a 5-, 6- or 7-membered carbocyclic ring or a 5-, 6- or 7-membered heterocyclic ring comprising at least one oxygen, nitrogen or sulfur atom.

The compounds according to the invention are fast dissociating $D_2$ receptor antagonists, an activity not attributed to any of the 6-phenyl-N-[4-piperidinyl]-3-pyridazinamine derivatives of J. Med. Chem. (1999), 42 (4), 730-741, nor any of the substituted N-[4-piperidinyl]-2-aminopyrimidines of Farmaco, Vol. 35, no. 11, 1980, pages 951-964. This property renders the compounds according to the invention especially suitable for use as a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation; pervasive developmental disorders; attention deficit disorders, attention-deficit/hyperactivity disorder, disruptive behaviour disorders; personality disorder of the paranoid type, personality disorder of the schizoid type, personality disorder of the schizotypical type; tic disorders, Tourette's syndrome; substance dependence; substance abuse; substance withdrawal; trichotillomania.

A skilled person can make a selection of compounds based on the experimental data provided in the Experimental Part hereinafter. Any selection of compounds is embraced within this invention.

A first group of compounds relates to compounds of Formula (I), wherein R, $R^3$ and $R^4$ are hydrogen.

A second group of compounds of Formula (I) are those wherein $R^2$ is hydrogen or methyl.

A third group of compounds are compounds of Formula (I) wherein $R^1$ is 3,5-difluorophenyl, 3,4,5-trifluorophenyl, 3-trifluoromethylphenyl, 3-fluoro-5-trifluoromethylphenyl or 3-fluoro-4-methylphenyl.

Compounds of Formula (I) are, for example,

6-[1-(3,4-Difluoro-benzyl)-piperidin-4-ylamino]-pyridazine-3-carbonitrile (E1),

6-[1-(4-Fluoro-benzyl)-piperidin-4-ylamino]-pyridazine-3-carbonitrile (E2),

6-[1-(4-Chloro-benzyl)-piperidin-4-ylamino]-pyridazine-3-carbonitrile (E3),

6-[1-(3-Fluoro-4-methyl-benzyl)-piperidin-4-ylamino]-pyridazine-3-carbonitrile (E4), 6-[1-(3-Fluoro-benzyl)-piperidin-4-ylamino]-pyridazine-3-carbonitrile (E5), 6-[1-(4-Methyl-benzyl)-piperidin-4-ylamino]-pyridazine-3-carbonitrile (E6), 6-[1-(4-Trifluoromethyl-benzyl)-piperidin-4-ylamino]-pyridazine-3-carbonitrile (E7), 6-[1-(3-Fluoro-4-trifluoromethyl-benzyl)-piperidin-4-ylamino]-pyridazine-3-carbonitrile (E8), 6-[1-(4-Fluoro-3-trifluoromethyl-benzyl)-piperidin-4-ylamino]-pyridazine-3-carbonitrile (E9), 6-[1-(4-Methyl-3-trifluoromethyl-benzyl)-piperidin-4-ylamino]-pyridazine-3-carbonitrile (E10), 6-[1-(3,5-Bis-trifluoromethyl-benzyl)-piperidin-4-ylamino]-pyridazine-3-carbonitrile (E11), 6-[1-(2-Fluoro-5-trifluoromethyl-benzyl)-piperidin-4-ylamino]-pyridazine-3-carbonitrile (E12), 6-[1-(3-Chloro-benzyl)-piperidin-4-ylamino]-pyridazine-3-carbonitrile (E13), 6-[1-(3-Chloro-4-trifluoromethoxy-benzyl)-piperidin-4-ylamino]-pyridazine-3-carbonitrile (E14), 6-[1-(3,5-Difluoro-benzyl)-piperidin-4-ylamino]-pyridazine-3-carbonitrile (E15), 6-[1-(3-Trifluoromethyl-benzyl)-piperidin-4-ylamino]-pyridazine-3-carbonitrile (E16), 6-[1-(3-Fluoro-5-trifluoromethyl-benzyl)-piperidin-4-ylamino]-pyridazine-3-carbonitrile (E17), 6-[1-(3,4,5-Trifluoro-benzyl)-piperidin-4-ylamino]-pyridazine-3-carbonitrile (E18), 6-[1-(3,5-Difluoro-benzyl)-piperidin-4-ylamino]-4,5-dimethyl-pyridazine-3-carbonitrile (E19), 6-[1-(3,5-Difluoro-benzyl)-piperidin-4-ylamino]-4-methyl-pyridazine-3-carbonitrile (E20), and 6-(1-Benzyl-piperidin-4-yl)-pyridazin-3-carbonitrile (D2).

Throughout this application, the term "$C_{1-4}$alkyl" when used alone and when used in combinations such as "$C_{1-4}$alkyloxy", "perfluoro$C_{1-4}$alkyl", "di$C_{1-4}$alkylamino", includes, for example, methyl, ethyl, propyl, butyl, 1-methylpropyl, 1,1-dimethylethyl, the term; "$C_{1-6}$alkyl" includes methyl, ethyl, propyl, butyl, 1-methylpropyl, 1,1-dimethylethyl, pentyl and hexyl; "perfluoro$C_{1-4}$alkyl" includes for example trifluoromethyl, pentafluoroethyl, heptafluoropropyl and nonafluorobutyl; $C_{3-8}$cycloalkyl includes cyclopropyl, cyclobutyl, cyclopentyl, cyclohexyl, cycloheptyl and cyclooctyl; $C_{5-7}$cycloalkenyl includes cyclopentenyl, cyclohexenyl and cycloheptenyl. The term halo includes fluoro, chloro, bromo and iodo.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, mandelic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, pamoic acid and mandelic acid. Conversely, said salts forms can be converted into the free forms by treatment with an appropriate base.

The term solvates refers to hydrates and alcoholates which the compounds of Formula (I) may form.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are embraced within the scope of this invention.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

Pharmacology

In order to find antipsychotic compounds active against positive symptoms and having an improved safety profile (low EPS incidence and no metabolic disorders), we have screened for compounds selectively interacting with the dopamine D2 receptor and dissociating fast from this receptor. Compounds were first screened for their D2 affinity in a binding assay using [$^3$H]spiperone and human D2L receptor cell membranes. The compounds showing an $IC_{50}$ less than 10 μM were tested in an indirect assay adapted from a method published by Josee E. Leysen and Walter Gommeren, Journal of Receptor Research, 1984, 4(7), 817-845, to evaluate their rate of dissociation.

Selected compounds E15, E16, E17 and E18 were further screened in a panel of more than 50 common G-protein coupled receptors (CEREP) and found to have a clean profile, that is to have low affinity for the tested receptors.

Most of the compounds have been further tested in in vivo models such as the "Inhibition of the Apomorphine induced agitation test in rats" subcutaneously and orally, and some were found to be orally bio-available and active.

In view of the aforementioned pharmacology of the compounds of Formula (I), it follows that they are suitable for use as a medicine, in particular for use as an antipsychotic. More especially the compounds are suitable for use as a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation; pervasive developmental disorders; attention deficit disorders, attention-deficit/hyperactivity disorder, disruptive behaviour disorders; personality disorder of the paranoid type, personality disorder of the schizoid type, personality disorder of the schizotypical type; tic disorders, Tourette's syndrome; substance dependence; substance abuse; substance withdrawal; trichotillomania.

To optimize treatment of patients suffering from a disorder as mentioned in the foregoing paragraph, the compounds of Formula (I) may be administered together with other psychotropic compounds. Thus, in the case of schizophrenia, negative and cognitive symptoms may be targeted.

The present invention also provides a method of treating warm-blooded animals suffering from such disorders, said method comprising the systemic administration of a therapeutic amount of a compound of Formula (I) effective in treating the above described disorders.

The present invention further provides a method of preventing any of the aforementioned disorders from occurring in warm-blooded animals prone to suffer from such disorders, said method comprising the systemic administration of a therapeutic amount of a compound of Formula (I) effective in preventing the above described disorders.

The present invention also relates to the use of compounds of Formula (I) as defined hereinabove for the manufacture of a medicament, in particular an antipsychotic medicament, more especially a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation; pervasive developmental disorders; attention deficit disorders, attention-deficit/hyperactivity disorder, disruptive behaviour disorders; personality disorder of the paranoid type, personality disorder of the schizoid type, personality disorder of the schizotypical type; tic disorders, Tourette's syndrome; substance dependence; substance abuse; substance withdrawal; trichotillomania.

Those of skill in the treatment and prevention of such diseases could determine the effective therapeutic daily amount from the test results presented hereinafter. An effective therapeutic daily amount would be from about 0.01 mg/kg to about 10 mg/kg body weight, more preferably from about 0.05 mg/kg to about 1 mg/kg body weight.

The invention also relates to a pharmaceutical composition comprising a pharmaceutically acceptable carrier and, as active ingredient, a therapeutically effective amount of a compound according to Formula (I).

Depending on the route of administration, the pharmaceutical composition will comprise from 0.05% to 99% by weight of the active ingredient, and from 1% to 99.95% by weight of a pharmaceutically acceptable carrier.

For ease of administration, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, an N-oxide form thereof and a prodrug thereof, or any subgroup or combination thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds according to the invention in pharmaceutical compositions.

Preparation

Compounds of Formula (I),

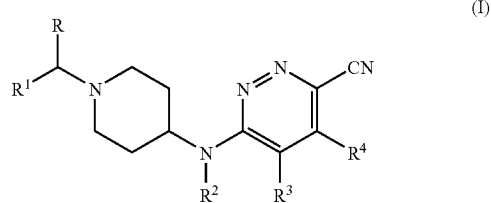

where R, $R^1$, $R^2$, $R^3$ and $R^4$ are as defined before, were prepared by reacting a compound of Formula (II),

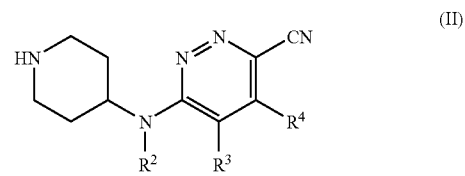

where $R^2$, $R^3$ and $R^4$ are as defined before, with a compound of Formula $R^1$—C(=O)—R (III-a), where R and $R^1$ are as defined before, in the presence of a suitable reducing agent such as sodium triacetoxyborohydride, a suitable acid catalyst, such as acetic acid, in a suitable reaction inert solvent such as 1,2-dichloroethane.

Compound of Formula (I), where R, $R^1$, $R^2$, $R^3$ and $R^4$ are as defined before, can also be prepared by reacting a compound of Formula (II), where $R^2$, $R^3$ and $R^4$ are as defined before, with a compound of Formula $R^1$—CHX—R (III-b), where R and $R^1$ are as defined before and X represents a halogen or a suitable leaving group, in the presence of a suitable base, such as diisopropylethylamine, in a suitable inert reaction solvent such as acetonitrile, at a convenient temperature, typically heating at 120° C. under microwave irradiation.

Compounds of Formula (II), where $R^2$, $R^3$ and $R^4$ are as defined before, were prepared by reacting a chloropyridazine derivative of Formula (IV)

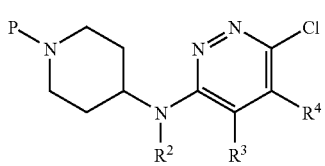

(IV)

where $R^2$, $R^3$ and $R^4$ are as defined before and P represents a suitable protecting group, such as a benzyl, with a cyanide salt, such as zinc cyanide, in the presence of a palladium catalyst, such as tetrakis(triphenylphosphine) palladium, in a suitable inert solvent, such as N,N-dimethylformamide, under suitable reaction conditions, typically heating at 160° C. under microwave irradiation, followed by deprotection of the protecting group, P, under suitable conditions, such as reaction with 1-chloroethyl-chloroformate, in the presence of a suitable base, such as diisopropylethylamine, in a suitable inert reaction solvent such as dichloromethane, for the benzyl group.

Compounds of Formula (IV), where $R^2$, $R^3$ and $R^4$ are as defined before and P represents a suitable protecting group, where prepared by reacting a compound of Formula (V),

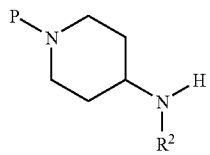

(V)

where $R^2$ is as defined before and P represents a suitable protecting group, such as benzyl, with a compound of Formula (VI)

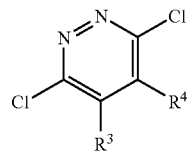

(VI)

where $R^3$ and $R^4$ are as defined before, in the presence of a suitable catalyst, such as potassium iodide, under suitable reaction conditions, such as in a melt.

Compounds of Formula (VI) are available commercially or are prepared by procedures similar to those described in WO 99/36407.

Compounds of Formula (I) where R, $R^1$, $R^2$, $R^3$ and $R^4$ are as defined before, can also be prepared reacting a 3-chloro-pyridazine of Formula (VII)

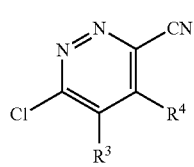

(VII)

wherein $R^3$ and $R^4$ are as defined before, with a piperidine derivative of Formula (VIII)

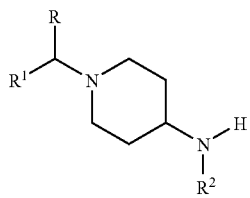

(VIII)

where R, $R^1$ and $R^2$ are as defined before, in the presence of a suitable base such as diisopropyethylamine, in a suitable solvent such as acetonitrile, at an elevated temperature.

Compounds of Formula (VIII), where R and $R^1$ are as defined before and $R^2$=H, were prepared by reacting piperidin-4-ylcarbamic acid tert-butyl ester (IX)

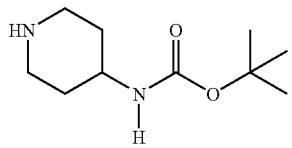

(IX)

with a compound of Formula $R^1$—CHX—R (III-b), where R and $R^1$ are as defined before and X represents a halogen or suitable leaving group, in the presence of a suitable base, such as diisopropylethylamine and in a suitable inert reaction solvent, such as dichloromethane, followed by deprotection of the tert-butyloxycarbonyl group in an intermediate of Formula (X), by treatment with an acid, such as trifluoroacetic acid, to give a compound of Formula (VIII) where $R^2$=H.

Compounds of Formula (VIII), where R and $R^1$ are as defined before and $R^2$=H could also be prepared by reacting piperidin-4-ylcarbamic acid tert-butyl ester (IX) with a compound of Formula $R^1$—C(=O)—R (III-a), where R and $R^1$ are as defined before, in the presence of a suitable reducing agent such as sodium triacetoxyborohydride, a suitable acid catalyst, such as acetic acid, in a suitable inert reaction solvent, such as 1,2-dichloroethane, followed by deprotection of the tert-butyloxycarbonyl group in an intermediate of Formula (X), by treatment with an acid, such as trifluoroacetic acid, to give a compound of Formula (VIII) where $R^2$=H.

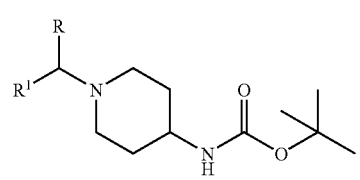

(X)

Compounds of Formula (VIII), where $R^2 \neq H$, could be prepared by reacting a compound of Formula (XI)

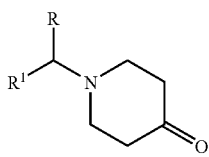

Where R and $R^1$ are as defined before, with an amine of Formula R—$NH_2$ (XII), in the presence of a suitable reducing agent, such as hydrogen, a suitable catalyst, such as palladium on carbon and in a suitable inert reaction solvent, such as ethanol.

Compounds of Formula (XI), where R and $R^1$ are as defined before, were prepared by reacting 4,4-ethylenedioxypiperidine (XIII)

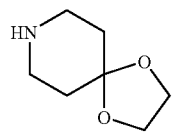

with a compound of Formula $R^1$—C(=O)—R (III-a), where R and $R^1$ are as defined before, in the presence of a suitable reducing agent, such as sodium triacetoxyborohydride, a suitable acid catalyst, such as acetic acid, in a suitable inert reaction solvent, such as 1,2-dichloroethane, followed by deprotection of an intermediate of Formula (XIV)

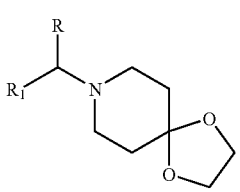

where R and $R^1$ are as defined before, by treatment with an acid, such as hydrochloric acid.

Compounds of Formula (VII) wherein $R^3$ and $R^4$ are as defined before, were prepared by reacting a 3-chloro-6-iodopyridazine of Formula (XV)

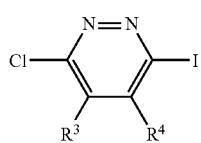

with a cyanide salt such as zinc or copper cyanide, in the presence of a palladium catalyst such as tetrakis(triphenylphosphine)palladium, in an inert solvent such as N,N-dimethylformamide or acetonitrile, under suitable reaction conditions, typically heating at 160° C. under microwave irradiation.

EXPERIMENTAL PART

Chemistry

Final purification of Examples (E1-E20) was carried out either by column chromatography on silica gel using the eluent described or by reversed phase preparative HPLC on a Hyperprep RP 18 BDS (Shandon) (8 μm, 200 mm, 250 g) column. Three mobile phases (mobile phase A: 90% 0.5% ammoniumacetate+10% acetonitrile; mobile phase B: methanol; mobile phase C: acetonitrile) were used to run a gradient method starting with 75% A and 25% B with a flow rate of 40 ml/min, (hold for 0.5 minutes at the same conditions followed with an increase of the flow rate to 80 ml/min in 0.01 minutes) to 50% B and 50% C in 41 minutes, to 100% C in 20 minutes and hold these conditions for 4 minutes.

$^1$H spectra were recorded on a Bruker DPX 360, DPX 400 or a Bruker AV-500 spectrometer. The chemical shifts are expressed in ppm relative to tetramethylsilane.

Description 1

(1-Benzyl-piperidin-4-yl)-(6-chloro-pyridazin-3-yl)-amine (D1)

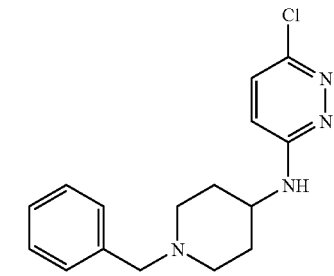

A mixture of 4-amino-1-benzylpiperidine (4 g, 21 mmol) and 3,6-dichloro-pyridazine (1.56 g, 10.5 mmol) was stirred for 1 h at 120° C., before n-butanol (10 ml) was added and the reaction mixture stirred for a further 1 h at 120° C. After addition of water and dichloromethane, the organic layer was separated, dried ($Na_2SO_4$), filtered and the solvent evaporated in vacuo. The residue was crystallized from acetonitrile and the resulting solid was filtered off and dried to yield D1 (1.3 g, 41%) as a solid. $C_{16}H_{19}ClN_4$ requires 302. Found 303 (MH$^+$); mp: 208.2-209.3° C.

$^1$H NMR (360 MHz, DMSO-$d_6$) δ 1.36-1.54 (m, 2H), 1.94 (d, J=10.98 Hz, 2H), 2.08 (t, J=10.79 Hz, 2H), 2.78 (d, J=11.71 Hz, 2H), 3.47 (s, 2H), 3.69-3.84 (m, 1H), 6.88 (d,

J=9.15 Hz, 1H), 7.03 (d, J=7.32 Hz, 1H), 7.22-7.28 (m, 1H), 7.28-7.34 (m, 4H), 7.34 (d, J=9.51 Hz, 1H).

Description D2

6-(1-Benzyl-piperidin-4-ylamino)-pyridazin-3-carbonitrile (D2)

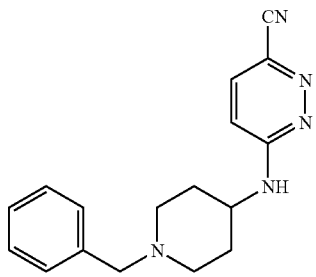 [SMILES: N#Cc1ccc(NC2CCN(Cc3ccccc3)CC2)nn1]

A mixture of (1-benzyl-piperidin-4-yl)-(6-chloro-pyridazin-3-yl)-amine (D1) (3 g, 9.9 mmol), zinc cyanide (2.09 g, 17.8 mmol) and tetrakis(triphenylphosphine)palladium(0) (2.74 g, 2.3 mmol) in N,N-dimethylformamide (30 ml) was heated at 160° C. for 30 min., under microwave irradiation (Milestone MW-oven). The solvent was then evaporated in vacuo and an aqueous solution of potassium carbonate (10%) and ethyl acetate were added. The organic phase was separated, dried ($Na_2SO_4$), filtered and the solvent evaporated in vacuo. The residue was purified by column chromatography (silica gel; 0 to 1.5% ammonia in methanol (7M)/dichloromethane) and then by HPLC to yield D2 (1.06 g, 36%) as a solid. $C_{17}H_{19}N_5$ requires 293. Found 294 ($MH^+$).

$^1H$ NMR (500 MHz, DMSO-$d_6$) δ 1.42-1.57 (m, 2H), 1.92 (d, J=10.40 Hz, 2H), 2.09 (t, J=10.84 Hz, 2H), 2.79 (d, J=11.27 Hz, 2H), 3.48 (s, 2H), 3.92 (br. s., 1H), 6.87 (d, J=8.96 Hz, 1H), 7.21-7.27 (m, 2H), 7.27-7.37 (m, 3H), 7.68 (d, J=9.54 Hz, 1H), 7.77 (br. s., 1H)

Description 3

6-(Piperidin-4-ylamino)-pyridazine-3-carbonitrile (D3)

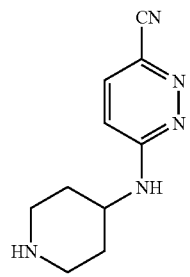 [SMILES: N#Cc1ccc(NC2CCNCC2)nn1]

1-chloroethyl chloroformate (2.9 g, 20 mmol) was added dropwise to a stirring mixture of 6-(1-benzyl-piperidin-4-yl)-pyridazin-3-carbonitrile (D2) (1.5 g, 5.1 mmol) and diisopropylethylamine (2.6 g, 20 mmol) in dichloromethane (50 ml) at 0° C. The reaction mixture was stirred at room temperature for 2 h and then the solvent evaporated in vacuo. Methanol (50 ml) was added to the residue and the mixture was refluxed for 2 h. The solvent was evaporated in vacuo and the residue purified by column chromatography (silica gel; 5-12% ammonia in methanol (7M)/dichloromethane). The desired fractions were collected and the solvent evaporated in vacuo to yield D3 (0.9 g, 90%) as a solid. $C_{10}H_{13}N_5$ requires 203. Found 204 ($MH^+$)

$^1H$ NMR (360 MHz, DMSO-$d_6$) δ 1.67-1.86 (m, 2H), 2.10 (dd, J=13.72, 3.48 Hz, 2H), 3.03 (td, J=12.81, 2.93 Hz, 2H), 3.32 (tt, J=13.17, 3.66 Hz, 2H), 4.24 (br. s., 1H), 7.00 (d, J=9.51 Hz, 1H), 7.75 (d, J=9.15 Hz, 1H), 8.33 (br. s., 1H), 8.23 (d, J=6.95 Hz, 1H)

Description 4

6-Chloro-pyridazine-3-carbonitrile (D4)

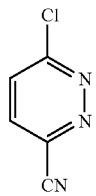

A mixture of 3-chloro-6-iodo-pyridazine (CAS 135034-10-5, 5.5 g, 22.9 mmol; Goodman, A. J.; Stanforth, S. P.; Tarbit, B. *Tetrahedron* (1999), 55 (52), 15067-15070) and copper cyanide (4 g, 44.7 mmol) in acetonitrile (30 ml) was stirred for 30 min. at 160° C., under microwave irradiation (Milestone MW-oven). The mixture was then poured into dichloromethane (200 ml), filtered over celite, and the solvent evaporated in vacuo. The residue was then purified by column chromatography (silica gel; dichloromethane/heptane 1:1 to 7:3) to yield D4 (2.84 g, 89%), as a solid.

$^1H$ NMR (400 MHz, $CDCl_3$) δ 7.65 (d, J=8.8 Hz, 1H), 7.75 (d, J=8.8 Hz, 1H).

Description 5

1-(3,5-Difluoro-benzyl)-piperidin-4-ylamine (D5)

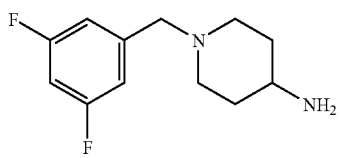 [SMILES: NC1CCN(Cc2cc(F)cc(F)c2)CC1]

A mixture of piperidin-4-ylcarbamic acid tert-butyl ester (5 g, 24.9 mmol), 3,5-difluorobenzyl bromide (2.9 ml, 22.7 mmol) and diisoproylethylamine (5.9 ml, 34.03 mmol) in dichloromethane (50 ml) was stirred at room temperature for 2 h. After this period, trifluoroacetic acid (32 ml) was added and the reaction mixture was stirred for a further 2 h. The solvent was evaporated in vacuo and a saturated solution of sodium carbonate was added. The mixture was extracted with dichloromethane, and the separated organic layers were dried (Na$_2$SO$_4$), filtered, and the solvent evaporated in vacuo to yield D5 (4.5 g, 90%) as a solid. C$_{12}$H$_{16}$F$_2$N$_2$ requires 226. Found 227 (MH$^+$)

Description 6

1-(3-Trifluoromethyl-benzyl)-piperidin-4-ylamine (D6)

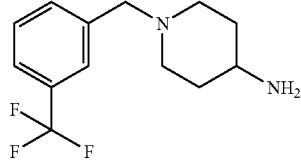 [SMILES: NC1CCN(Cc2cccc(C(F)(F)F)c2)CC1]

A mixture of piperidin-4-ylcarbamic acid tert-butyl ester (2.5 g, 12.4 mmol), 3-(trifluoromethyl)benzyl bromide (1.7 ml, 11.3 mmol) and diisoproylethylamine (2.9 ml, 16.9 mmol) in dichloromethane (25 ml) was stirred at room temperature for 2 h. After this period, trifluoroacetic acid (32 ml) was added and the reaction mixture was stirred for a further 2 h. The solvent was evaporated in vacuo and a saturated solution of sodium carbonate was added. The mixture was extracted with dichloromethane and the separated organic layers were dried (Na$_2$SO$_4$), filtered, and the solvent evaporated in vacuo. The residue was purified by column chromatography (silica gel; 5-10% ammonia in methanol (7 M)/dichloromethane) to yield D6 (1.9 g, 60%) as a solid. C$_{13}$H$_{12}$F$_3$N$_2$ requires 258. Found 259 (MH$^+$)

Description 7

1-(3-Fluoro-5-trifluoromethyl-benzyl)-piperidin-4-ylamine (D7)

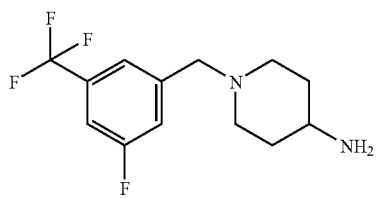 [SMILES: NC1CCN(Cc2cc(F)cc(C(F)(F)F)c2)CC1]

A mixture of piperidin-4-ylcarbamic acid tert-butyl ester (4 g, 20 mmol), 3-fluoro-5-(trifluoromethyl)benzyl bromide (4.6 g, 18.1 mmol) and diisoproylethylamine (4.7 ml, 27.1 mmol) in dichloromethane (25 ml) was stirred at room temperature for 2 h. After this period, trifluoroacetic acid (32 ml) was added and the reaction mixture was stirred for a further 2 h. The solvent was evaporated in vacuo and a saturated solution of sodium carbonate was added. The mixture was extracted with dichloromethane and the separated organic layer was dried (Na$_2$SO$_4$), filtered, and the solvent evaporated in vacuo to yield D7 (4 g, 80%) as a solid. C$_{13}$H$_{16}$F$_4$N$_2$ requires 276. Found 277 (MH$^+$)

Description 8

1-(3,4,5-Trifluoro-benzyl)-piperidin-4-ylamine (D8)

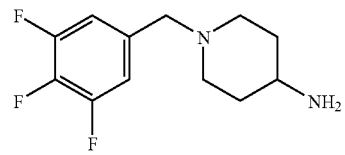

A mixture of piperidin-4-ylcarbamic acid tert-butyl ester (2.5 g, 12.4 mmol), 3,4,5-trifluorobenzyl bromide (2.5 g, 11.3 mmol) and diisoproylethylamine (2.9 ml, 16.9 mmol) in dichloromethane (25 ml) was stirred at room temperature for 2 h. After this period, trifluoroacetic acid (15.6 ml) was added and the reaction was stirred for a further 2 h. The solvent was evaporated in vacuo and a saturated solution of sodium carbonate was added. The mixture was extracted with dichloromethane and the separated organic layers were dried (Na$_2$SO$_4$), filtered, and the solvent evaporated in vacuo to yield D8 (2.9 g, 96%) as a solid. C$_{12}$H$_{15}$F$_3$N$_2$ requires 244. Found 245 (MH$^+$)

Description 9

3,6-Dichloro-4,5-dimethyl-pyridazine (D9)

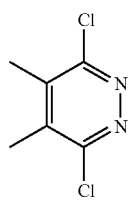

A mixture of 6-hydroxy-4,5-dimethyl-2H-pyridazin-3-one (2.56 g, 18 mmol) (prepared by a procedure similar to that described in WO 99/36407), phosphorus oxychloride (8 ml) and diisopropylethylamine (4 ml) was stirred at 160° C. for 20 min., under microwave irradiation (Biotage MW-oven). The solvent was then partially evaporated in vacuo and remaining material poured into a mixture of cold water, saturated sodium hydrogen carbonate and dichloromethane. The mixture was then basified with portions of sodium hydrogen carbonate until there was no more CO$_2$ evolution. The organic layer was separated, dried (Na$_2$SO$_4$), filtered and the solvent evaporated in vacuo. The residue was purified by column chromatography (dichloromethane/heptane 1/1 to 10/0) to yield D9 (1.7 g, 53%) as a solid. $C_6H_6Cl_2N_2$ requires 176. Found 177 (MH⁺)

Description 10

3-Chloro-6-iodo-4,5-dimethyl-pyridazine (D10)

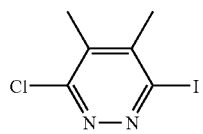

A mixture of D9 (0.2 g, 1.13 mmol), sodium iodide (0.420 g, 2.8 mmol) and hydroiodic acid (57 wt. % in water, 2 ml) was stirred at 120° C. for 10 min., under microwave irradiation. The mixture was then poured into an aqueous saturated solution of sodium carbonate, $Na_2S_2O_3$, water and dichloromethane. The organic phase was separated, filtered over cotton, and the solvent evaporated in vacuo. The residue was purified by column chromatography (dichloromethane/heptane 1:1 to 8:2) to yield D10 (0.235 g, 77%) as a solid. $C_6H_6ClIN_2$ requires 268. Found 269 (MH⁺).

Description 11

6-Chloro-4,5-dimethyl-pyridazine-3-carbonitrile (D11)

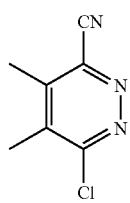

A mixture of D10 (0.225 g, 0.84 mmol), copper cyanide (0.15 g, 1.67 mmol) in acetonitrile (2 ml) was stirred at 160° C. for 20 min., under microwave irradiation. Dichloromethane was then added and the mixture filtered over celite. The solvent was evaporated in vacuo and the residue purified by column chromatography (silica gel; dichloromethane/heptane 1:1 to 7:3) to yield D11 (0.120 g, 85%) as a solid. $C_7H_6ClN_3$ requires 167. Found 166 (MH⁻).

Example 7

6-[1-(4-Trifluoromethyl-benzyl)-piperidin-4-ylamino]-pyridazine-3-carbonitrile (E7)

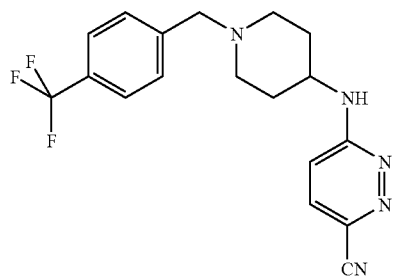 [SMILES: N#Cc1ccc(NC2CCN(Cc3ccc(C(F)(F)F)cc3)CC2)nn1]

To a mixture of 6-(piperidin-4-ylamino)-pyridazine-3-carbonitrile (D3) (0.15 g, 0.7 mmol) and α,α,α-trifluoro-p-tolualdehyde (0.15 ml, 1.1 mmol) in dichloromethane (2 ml), was added sodium triacetoxyborohydride (0.232 g, 1.1 mmol) and acetic acid (0.041 ml). The reaction mixture was then stirred at room temperature for 18 h. A saturated solution of sodium hydrogen carbonate was then added and the organic layer was separated, dried ($Na_2SO_4$), filtered and the solvent evaporated in vacuo. The residue was purified by HPLC. The desired fractions were collected and the solvent was evaporated in vacuo to yield E7 (0.101 g, 38%) as a solid. $C_{18}H_{18}F_3N_5$ requires 361. Found 362 (MH⁺); mp: 243.1° C.
¹H NMR (500 MHz, CDCl₃) δ 1.56-1.65 (m, 2H), 2.09 (d, J=11.85 Hz, 2H), 2.22 (t, J=10.55 Hz, 2H), 2.85 (d, J=11.85 Hz, 2H), 3.58 (s, 2H), 3.93 (br. s., 1H), 5.14 (br. s., 1H), 6.60 (d, J=9.25 Hz, 1H), 7.40 (d, J=9.25 Hz, 1H), 7.45 (d, J=7.80 Hz, 2H), 7.58 (d, J=8.09 Hz, 2H).

Example 13

6-[1-(3-Chloro-benzyl)-piperidin-4-ylamino]-pyridazine-3-carbonitrile (E13)

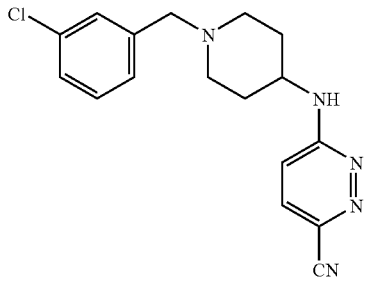 [SMILES: N#Cc1ccc(NC2CCN(Cc3cccc(Cl)c3)CC2)nn1]

A mixture of 6-(piperidin-4-ylamino)-pyridazine-3-carbonitrile (D3) (0.150 g, 0.74 mmol), 3-chlorobenzyl bromide (0.102 ml, 0.78 mol) and diisopropylethylamine (0.196 ml, 1.11 mol) in acetonitrile (2 ml) was stirred at 120° C. for 5 min., under microwave irradiation (Biotage MW-oven). The reaction mixture was then diluted with dichloromethane and extracted with a saturated solution of sodium carbonate. The organic layers were separated, dried ($Na_2SO_4$), filtered and the solvent evaporated in vacuo. The residue was then purified by column chromatography (silica gel; 0-2.5% ammonia in methanol (7 M)/dichloromethane). The desired fractions were collected and evaporated in vacuo, and the residue triturated with diisopropylether to yield E13 (0.095 g, 39%) as a white solid. $C_{17}H_{18}ClN_5$ requires 327. Found 328 (MH$^+$); mp: 151° C.

$^1$H NMR (400 MHz, CDCl$_3$) δ 1.52-1.70 (m, 2H) 2.08 (d, J=12.02 Hz, 2H), 2.19 (t, J=11.30 Hz, 2H), 2.85 (d, J=11.82 Hz, 2H), 3.50 (s, 2H), 3.91 (br. s., 1H), 5.23 (br. s., 1H), 6.62 (d, J=9.33 Hz, 1H), 7.17-7.21 (m, 1H), 7.21-7.28 (m, 2H), 7.34 (br. s., 1H), 7.41 (d, J=9.33 Hz, 1H)

Example 15

6-[1-(3,5-Difluoro-benzyl)-piperidin-4-ylamino]-pyridazine-3-carbonitrile (E15)

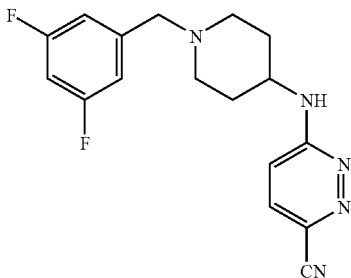 [SMILES: N#Cc1ccc(NC2CCN(Cc3cc(F)cc(F)c3)CC2)nn1]

A mixture of 6-chloro-pyridazine-3-carbonitrile (D4) (1.74 g, 12.46 mmol), 1-(3,5-difluoro-benzyl)-piperidin-4-ylamine (D5) (2.35 g, 10.386 mmol) and diisopropylethylamine (2.71 ml, 15.58 mmol) in acetonitrile (30 ml) was stirred at 120° C. for 40 min., under microwave irradiation (Milestone MW-oven). Dichloromethane, water and a saturated solution of sodium carbonate were then added. The organic layers were filtered over cotton, evaporated in vacuo and the residue was purified by column chromatography (silica gel; 0-1.5% ammonia in methanol (7 M)/dichloromethane). The desired fractions were collected and evaporated in vacuo. The residue was precipitated in heptane to yield E15 (2.065 g, 60%) as a solid. $C_{17}H_{17}F_2N_5$ requires 329. Found 330 (MH$^+$); mp: 187.9° C.

$^1$H NMR (500 MHz, CDCl$_3$) δ 1.55-1.69 (m, 2H), 2.10 (d, J=11.85 Hz, 2H), 2.21 (t, J=11.42 Hz, 2H), 2.85 (d, J=11.85 Hz, 2H), 3.50 (s, 2H), 3.94 (br. s., 1H), 5.22 (br. s., 1 H), 6.62 (d, J=9.54 Hz, 1H), 6.69 (tt, J=8.92, 2.20 Hz, 1H), 6.83-6.93 (m, 2H), 7.41 (d, J=9.25 Hz, 1H).

Example 16

6-[1-(3-Trifluoromethyl-benzyl)-piperidin-4-ylamino]-pyridazine-3-carbonitrile (E16)

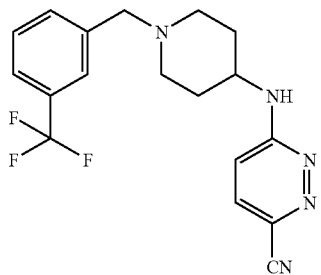 [SMILES: N#Cc1ccc(NC2CCN(Cc3cccc(C(F)(F)F)c3)CC2)nn1]

A mixture of 6-chloro-pyridazine-3-carbonitrile (D4) (0.130 g, 0.931 mmol), 1-(3-trifluoromethyl-benzyl)-piperidin-4-ylamine (D6) (0.241 g, 0.931 mmol) and diisopropylethylamine (0.243 ml, 1.4 mmol) in acetonitrile (3 ml) was stirred at 120° C. for 30 min., under microwave irradiation (Biotage MW-oven). Dichloromethane and water were added, and then the mixture washed with a saturated solution of sodium carbonate. The organic phase was filtered over cotton and the solvent was evaporated in vacuo. The residue was purified by column chromatography (silica gel; 0-2% ammonia in methanol (7M)/dichloromethane) to yield E16 (0.215 g, 64%) as a solid. $C_{18}H_{18}F_3N_5$ requires 361. Found 362 (MH$^+$); mp: 170.3° C.

$^1$H NMR (400 MHz, CDCl$_3$) δ 1.61 (qd, J=11.20, 3.52 Hz, 2H), 2.09 (d, J=12.44 Hz, 2H), 2.22 (td, J=11.20, 2.07 Hz, 2H), 2.86 (d, J=12.02 Hz, 2H), 3.58 (s, 2H), 3.93 (br. s., 1H), 5.18 (br. s., 1H), 6.61 (d, J=9.33 Hz, 1H), 7.41 (d, J=9.33 Hz, 1H), 7.45 (d, J=7.67 Hz, 1H), 7.49-7.55 (m, 2H), 7.60 (br. s., 1H).

Example 17

6-[1-(3-Fluoro-5-trifluoromethyl-benzyl)-piperidin-4-ylamino]-pyridazine-3-carbonitrile (E17)

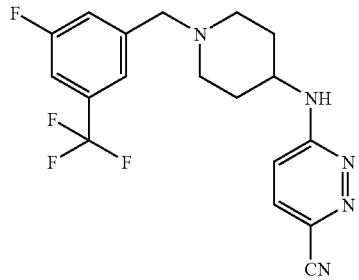 [SMILES: N#Cc1ccc(NC2CCN(Cc3cc(F)cc(C(F)(F)F)c3)CC2)nn1]

A mixture of 6-chloro-pyridazine-3-carbonitrile (D4) (1.39 g, 9.95 mmol), 1-(3-fluoro-5-trifluoromethyl-benzyl)-piperidin-4-ylamine (D7) (2.5 g, 9.04 mmol) and diisopropylethylamine (2.63 ml, 14.92 mmol) in acetonitrile (2 ml) was stirred at 120° C. for 30 min, under microwave irradiation ((Biotage MW-oven). The mixture was then diluted with dichloromethane (50 ml) and extracted with a saturated solution of sodium carbonate. The organic layer was separated, dried (Na$_2$SO$_4$), filtered, evaporated in vacuo and the residue purified by column chromatography (silica gel; 0-2.5% ammonia in methanol (7M)/dichloromethane). The desired fractions were collected and evaporated in vacuo. The residue precipitated from diisopropylether to yield E17 (2.76 g, 73%) as a solid. C$_{18}$H$_{17}$F$_4$N$_5$ requires 379. Found 380 (MH$^+$); mp: 151.4° C.

$^1$H NMR (500 MHz, CDCl$_3$) δ 1.56-1.70 (m, 2H), 2.11 (d, J=11.85 Hz, 2H), 2.24 (t, J=11.27 Hz, 2H), 2.85 (d, J=11.56 Hz, 2H), 3.56 (s, 2H), 3.96 (br. s., 1H), 5.24 (br. s., 1H), 6.63 (d, J=9.25 Hz, 1H), 7.22 (d, J=8.38 Hz, 1H), 7.28 (d, J=9.25 Hz, 1H), 7.39 (s, 1H), 7.42 (d, J=9.25 Hz, 1H).

Example 18

6-[1-(3,4,5-Trifluoro-benzyl)-piperidin-4-ylamino]-pyridazine-3-carbonitrile (E18)

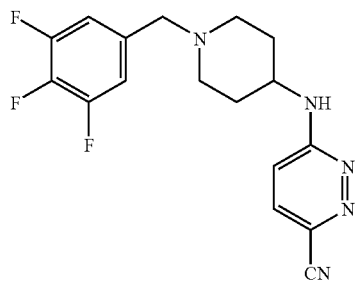 [SMILES: N#Cc1ccc(NC2CCN(Cc3cc(F)c(F)c(F)c3)CC2)nn1]

A mixture of 6-chloro-pyridazine-3-carbonitrile (D4) (1.32 g, 9.46 mmol), 1-(3,4,5-trifluoro-benzyl)-piperidin-4-ylamine (D8) (2.10 g, 8.6 mmol) and diisopropylethylamine (2.25 ml, 12.9 mmol) in acetonitrile (12 ml) was stirred at 120° C. for 20 min., under microwave irradiation (Milestone MW-oven). Dichloromethane, water and a saturated solution of sodium carbonate were then added. The organic layers were filtered over cotton, evaporated in vacuo and the residue was purified by column chromatography (silica gel; 0-2% ammonia in methanol (7M)/dichloromethane). The desired fractions were collected and evaporated in vacuo. The residue was precipitated from diisopropyl ether to yield E18 (2.210 g, 74%) as a solid. C$_{17}$H$_{16}$F$_3$N$_5$ requires 347. Found 348 (MH$^+$); mp: 185° C.

$^1$H NMR (500 MHz, CDCl$_3$) δ 1.52-1.69 (m, 2H), 2.10 (d, J=12.14 Hz, 2H), 2.21 (t, J=10.69 Hz, 2H), 2.83 (d, J=11.85 Hz, 2H), 3.44 (s, 2H), 3.95 (br. s., 1H), 5.17 (br. s., 1H), 6.62 (d, J=9.25 Hz, 1H), 6.89-7.07 (m, 2H), 7.41 (d, J=9.25 Hz, 1H).

Example 19

6-[1-(3,5-Difluoro-benzyl)-piperidin-4-ylamino]-4,5-dimethyl-pyridazine-3-carbonitrile (E19)

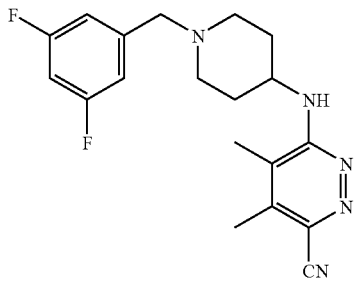 [SMILES: Cc1c(C#N)nnc(NC2CCN(Cc3cc(F)cc(F)c3)CC2)c1C]

A mixture of 6-chloro-4,5-dimethyl-pyridazine-3-carbonitrile (D11) (0.120 g, 0.72 mmol), 1-(3,5-difluoro-benzyl)-piperidin-4-ylamine (D5) (0.194 g, 0.86 mmol) and diisopropylethylamine (0.188 ml, 1.08 mmol) in acetonitrile was stirred at 180° C. for 20 min., under microwave irradiation (Biotage MW-oven), and then again at 180° C. for additional 30 min. Dichloromethane, water and a saturated solution of sodium carbonate were then added. The organic phase was separated, filtered over cotton and evaporated in vacuo. The residue was purified by column chromatography (silica gel; 0-1% ammonia in methanol (7M)/dichloromethane). The desired fractions were collected and the solvent evaporated in vacuo to yield E19 (0.108 g, 42%) as a solid. C$_{19}$H$_{21}$F$_2$N$_5$ requires 357. Found 358 (MH$^+$).

$^1$H NMR (400 MHz, CDCl$_3$) δ 1.57 (qd, J=11.58, 3.63 Hz, 2H), 2.07 (s, 3H), 2.15 (d, J=12.65 Hz, 2H), 2.18-2.27 (m, 2H), 2.41 (s, 3H), 2.85 (d, J=11.82 Hz, 2H), 3.49 (s, 2H), 4.23-4.39 (m, 1H), 4.46 (d, J=7.46 Hz, 1H), 6.69 (tt, J=8.91, 2.28 Hz, 1H), 6.82-6.95 (m, 2H)

For a number of compounds, melting points were determined in open capillary tubes on a Mettler FP62 apparatus. Melting points were measured with a temperature gradient of 3 or 10° C./minute. Maximum temperature was 300° C. The melting points were read from a digital display and were obtained with experimental uncertainties that are commonly associated with this analytical method.

The following additional examples (E1-E6, E8-E12 and E14) were prepared from D3 and the corresponding aldehydes or alkylating agents, by procedures similar to those described for Examples E7 and E13.

| Example | R¹ | Melting Point (°C.) | Molecular Formula | M. Wt | MH+ |
|---|---|---|---|---|---|
| E1 | 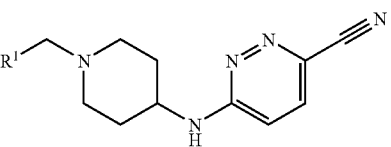 | 189.86 | $C_{17}H_{17}F_2N_5$ | 329 | 330 |
| E2 | 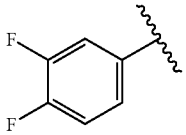 [SMILES: *c1ccc(F)c(F)c1] | 187.44 | $C_{17}H_{18}FN_5$ | 311 | 312 |
| E3 | 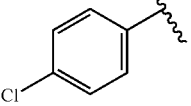 | 209.77 | $C_{17}H_{18}ClN_5$ | 327 | 328 |
| E4 | 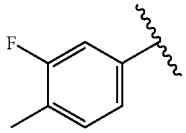 [SMILES: *c1ccc(C)c(F)c1] | 171.84 | $C_{18}H_{20}FN_5$ | 325 | 326 |
| E5 | 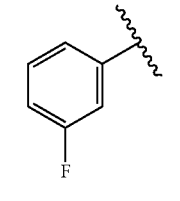 [SMILES: *c1cccc(F)c1] | 190.3 | $C_{17}H_{18}FN_5$ | 311 | 312 |
| E6 | 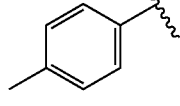 | 191.62 | $C_{18}H_{21}N_5$ | 307 | 308 |
| E7 | 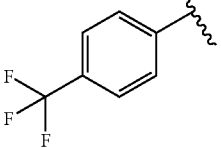 | 243.1 | $C_{18}H_{18}F_3N_5$ | 361 | 362 |
| E8 | 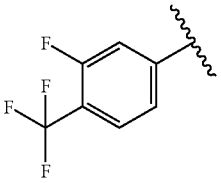 [SMILES: *c1ccc(C(F)(F)F)c(F)c1] | 178.6 | $C_{18}H_{17}F_4N_5$ | 379 | 380 |

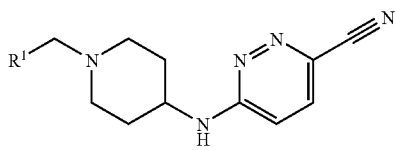
| Example | R¹ | Melting Point (° C.) | Molecular Formula | M. Wt | MH+ |
|---|---|---|---|---|---|
| E9 | 4-F, 3-CF₃-phenyl | 183.1 | $C_{18}H_{17}F_4N_5$ | 379 | 380 |
| E10 | 4-Me, 3-CF₃-phenyl | 187.3 | $C_{19}H_{20}F_3N_5$ | 375 | 376 |
| E11 | 3,5-bis(CF₃)-phenyl | 125 | $C_{19}H_{17}F_6N_5$ | 429 | 430 |
| E12 | 2-F, 5-CF₃-phenyl | 142.5 | $C_{18}H_{17}F_4N_5$ | 379 | 380 |
| E13 | 3-Cl-phenyl | 151 | $C_{17}H_{18}ClN_5$ | 327 | 328 |
| E14 | 3-OCF₃, 4-Cl-phenyl | — | $C_{18}H_{17}ClF_3N_5O$ | 411 | 412 |

| Example | R¹ | Melting Point (° C.) | Molecular Formula | M. Wt | MH+ |
|---|---|---|---|---|---|
| E15 | 3,5-difluorophenyl | 187.9 | $C_{17}H_{17}F_2N_5$ | 329 | 330 |
| E16 | 3-(trifluoromethyl)phenyl | 170.3 | $C_{18}H_{18}F_3N_5$ | 361 | 362 |
| E17 | 3-fluoro-5-(trifluoromethyl)phenyl | 151.4 | $C_{18}H_{17}F_4N_5$ | 379 | 380 |
| E18 | 3,4,5-trifluorophenyl | 185 | $C_{17}H_{16}F_3N_5$ | 347 | 348 |

The following Example (E20) was prepared by procedures similar to that described for Example E19.

| Example | R¹ | R³ | R⁴ | Molecular Formula | M. Wt | MH+ |
|---|---|---|---|---|---|---|
| E19 | 3,5-difluorophenyl | Me | Me | $C_{19}H_{21}F_2N_5$ | 357 | 358 |
| E20 | 3,5-difluorophenyl | H | Me | $C_{18}H_{19}F_2N_5$ | 343 | 344 |

The mass of some compounds was recorded with LCMS (liquid chromatography mass spectrometry). The method that was used is described below:

The HPLC measurement was performed using a HP 1100 from Agilent Technologies comprising a pump (quaternary or binary) with degasser, an autosampler, a column oven, a diode-array detector (DAD) and a column as specified in the respective methods below. Flow from the column was split to a MS spectrometer. The MS detector was configured with an electrospray ionization source. Nitrogen was used as the nebulizer gas. The source temperature was maintained at 140° C. Data acquisition was performed with MassLynx-Openlynx software. Reversed phase HPLC was carried out on an ACE-C18 column (3.0 μm, 4.6×30 mm) from Advanced Chromatography Technologies, with a flow rate of 1.5 ml/min, at 40° C. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 μl. High-resolution mass spectra (Time of Flight, TOF) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucine-Enkephaline was the standard substance used for the lock mass calibration.

| Example | $R_t$ (minutes) | (MH$^+$) |
| --- | --- | --- |
| E14 | 4.89 | 412 |
| E19 | 4.33 | 358 |
| E20 | 4.10 | 344 |

The following chemical names refer to the Example Numbers:

6-[1-(3,4-Difluoro-benzyl)-piperidin-4-ylamino]-pyridazine-3-carbonitrile (E1),
6-[1-(4-Fluoro-benzyl)-piperidin-4-ylamino]-pyridazine-3-carbonitrile (E2),
6-[1-(4-Chloro-benzyl)-piperidin-4-ylamino]-pyridazine-3-carbonitrile (E3),
6-[1-(3-Fluoro-4-methyl-benzyl)-piperidin-4-ylamino]-pyridazine-3-carbonitrile (E4),
6-[1-(3-Fluoro-benzyl)-piperidin-4-ylamino]-pyridazine-3-carbonitrile (E5),
6-[1-(4-Methyl-benzyl)-piperidin-4-ylamino]-pyridazine-3-carbonitrile (E6),
6-[1-(4-Trifluoromethyl-benzyl)-piperidin-4-ylamino]-pyridazine-3-carbonitrile (E7),
6-[1-(3-Fluoro-4-trifluoromethyl-benzyl)-piperidin-4-ylamino]-pyridazine-3-carbonitrile (E8),
6-[1-(4-Fluoro-3-trifluoromethyl-benzyl)-piperidin-4-ylamino]-pyridazine-3-carbonitrile (E9),
6-[1-(4-Methyl-3-trifluoromethyl-benzyl)-piperidin-4-ylamino]-pyridazine-3-carbonitrile (E10),
6-[1-(3,5-Bis-trifluoromethyl-benzyl)-piperidin-4-ylamino]-pyridazine-3-carbonitrile (E11),
6-[1-(2-Fluoro-5-trifluoromethyl-benzyl)-piperidin-4-ylamino]-pyridazine-3-carbonitrile (E12),
6-[1-(3-Chloro-benzyl)-piperidin-4-ylamino]-pyridazine-3-carbonitrile (E13),
6-[1-(3-Chloro-4-trifluoromethoxy-benzyl)-piperidin-4-ylamino]-pyridazine-3-carbonitrile (E14),
6-[1-(3,5-Difluoro-benzyl)-piperidin-4-ylamino]-pyridazine-3-carbonitrile (E15),
6-[1-(3-Trifluoromethyl-benzyl)-piperidin-4-ylamino]-pyridazine-3-carbonitrile (E16),
6-[1-(3-Fluoro-5-trifluoromethyl-benzyl)-piperidin-4-ylamino]-pyridazine-3-carbonitrile (E17),
6-[1-(3,4,5-Trifluoro-benzyl)-piperidin-4-ylamino]-pyridazine-3-carbonitrile (E18),
6-[1-(3,5-Difluoro-benzyl)-piperidin-4-ylamino]-4,5-dimethyl-pyridazine-3-carbonitrile (E19), and
6-[1-(3,5-Difluoro-benzyl)-piperidin-4-ylamino]-4-methyl-pyridazine-3-carbonitrile (E20).

Pharmacology

In Vitro Binding Affinity for Human $D2_L$ Receptor

Frozen membranes of human Dopamine $D2_L$ receptor-transfected CHO cells were thawed, briefly homogenised using an Ultra-Turrax T25 homogeniser and diluted in Tris-HCl assay buffer containing NaCl, $CaCl_2$, $MgCl_2$, KCl (50, 120, 2, 1, and 5 mM respectively, adjusted to pH 7.7 with HCl) to an appropriate protein concentration optimised for specific and non-specific binding. Radioligand [$^3$H]Spiperone (NEN, specific activity ~70 Ci/mmol) was diluted in assay buffer at a concentration of 2 nmol/L. Prepared radioligand (50 μl), along with 50 μl of either the 10% DMSO control, Butaclamol ($10^{-6}$ mol/l final concentration), or compound of interest, was then incubated (30 min, 37° C.) with 400 μl of the prepared membrane solution. Membrane-bound activity was filtered through a Packard Filtermate harvester onto GF/B Unifilterplates and washed with ice-cold Tris-HCl buffer (50 mM; pH 7.7; 6×0.5 ml). Filters were allowed to dry before adding scintillation fluid and counting in a Topcount scintillation counter. Percentage specific bound and competition binding curves were calculated using S-Plus software (Insightful).

| Example | $pIC_{50}$ |
| --- | --- |
| D2 | 5.53 |
| E1 | 5.39 |
| E2 | 5.49 |
| E3 | 5.98 |
| E4 | 6.39 |
| E5 | 5.22 |
| E6 | 6.02 |
| E7 | <5 |
| E8 | 5.12 |
| E9 | 5.17 |
| E10 | 5.19 |
| E11 | <5 |
| E12 | 5.20 |
| E13 | 5.49 |
| E14 | <5 |
| E15 | 5.18 |
| E16 | 5.85 |
| E17 | 5.52 |
| E18 | 5.24 |
| E19 | 5.74 |
| E20 | 5.21 |

Fast Dissociation

Compounds showing an $IC_{50}$ less than 10 μM were tested in an indirect assay adapted from a method published by Josee E. Leysen and Walter Gommeren, Journal of Receptor Research, 1984, 4(7), 817-845, to evaluate their rate of dissociation. Compounds at a concentration of 4 times their $IC_{50}$ were first incubated for one hour with human D2L receptor cell membranes in a volume of 2 ml at 25° C., then filtered over glass-fibre filter under suction using a 40 well multividor. Immediately after, the vacuum was released. 0.4 ml of pre-warmed buffer (25° C.) containing 1 nM [$^3$H]spiperone was added on the filter for 5 minutes. The incubation was stopped by initiating the vacuum and immediate rinsing with 2×5 ml of ice-cold buffer. The filter-bound radioactivity was measured in a liquid scintillation spectrometer. The principle of the assay is based on the assumption that the faster a compound dissociates from the D2 receptor, the faster [$^3$H] spiperone binds to the D2 receptor. For example, when D2 receptors are incubated with clozapine at the concentration of 1850 nM (4×IC$_{50}$), [$^3$H]spiperone binding is equivalent to 60-70% of its total binding capacity (measured in absence of drug) after 5 min incubation on filter. When incubated with other antipsychotics, [$^3$H]spiperone binding varies between 20 and 50%. Since clozapine was included in each filtration run, tested compounds were considered fast dissociating D2 antagonists if they were dissociating as fast or faster than clozapine. All compounds tested so far had a dissociation rate faster than that of clozapine, i.e. >50%.

| Example | % Dissociation |
|---------|----------------|
| E3      | 87%            |
| E4      | 82%            |
| E6      | 84%            |
| E7      | 93.50%         |
| E8      | 89.50%         |
| E15     | 93.50%         |
| E16     | 79.50%         |
| E17     | 73%            |
| E18     | 95%            |
| E19     | 83.66%         |

Inhibition of the Apomorphine Induced Agitation Test in Rats

Male Wiga Wistar rats (180-280 g) were administered test compound (sc: subcutaneously; po: orally; n=3 per dose; dose=0.16, 0.63 and 2.5 mg/kg) or solvent and then challenged with apomorphine (1.0 mg/kg, i.v.) at 30 min. The effects of the test compound on the behavioral changes were evaluated according to all-or-none criteria based on the distribution of results in a large series of control data obtained in solvent-pretreated rats.

Apomorphine (1.0 mg/kg, i.v.)-induced agitation, stereotypy (compulsive sniffing, licking, chewing), was scored every 5 min over the first hour after injection of apomorphine. The score system was: (3) pronounced, (2) moderate, (1) slight, and (0) absent. Criteria for drug-induced inhibition of agitation: fewer than 6 scores of 3 (0.16% false positives; n=2966), fewer than 6 scores of ≧2 (0.0% false positives) or fewer than 7 scores of ≧1 (0.0% false positives). The table below gives the lowest active dose at which 3 out of 3 rats tested met one of the criteria for drug-induced inhibition of agitation.

| Example | sc Dose mg/kg | po Dose mg/kg |
|---------|---------------|---------------|
| D2      | 2.5           |               |
| E1      | 2.5           |               |
| E2      | 0.63          | 0.63          |
| E3      | 0.63          |               |
| E4      | 0.16          |               |
| E5      | 2.5           |               |
| E6      | 2.5           |               |
| E7      | 0.63          | 2.5           |
| E8      | 2.5           | 2.5           |
| E9      | 2.5           |               |
| E10     | >2.5          |               |
| E12     | >2.5          |               |
| E13     | 2.5           |               |
| E15     | 0.63          | 1.25          |
| E16     | 0.63          | 0.63          |
| E17     | 0.63          | 1.25          |
| E18     | 0.63          | 1.25          |
| E19     | 0.63          | 2.5           |
| E20     | 2.5           |               |

The invention claimed is:

1. A compound of formula (I)

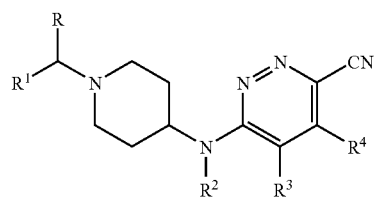

or a pharmaceutically acceptable salt thereof, or a stereoisomeric form thereof, wherein R is hydrogen or $C_{1-6}$alkyl;

$R^1$ is phenyl; phenyl substituted with 1, 2 or 3 substituents each independently selected from the group consisting of hydrogen, halo, cyano, $C_{1-4}$ alkyl, $C_{1-4}$alkyloxy, perfluoro$C_{1-4}$alkyl, and trifluoromethoxy; thienyl; thienyl substituted with 1 or 2 substituents selected from the group consisting of halo and $C_{1-4}$alkyl; $C_{1-4}$alkyl; $C_{1-4}$alkyl substituted with hydroxyl, $C_{3-8}$cycloalkyl or $C_{5-7}$cycloalkenyl; $C_{3-8}$cycloalkyl; or $C_{5-7}$cycloalkenyl;

$R^2$ is hydrogen or $C_{1-6}$alkyl;

$R^3$ and $R^4$ each independently are hydrogen, $C_{1-4}$ alkyl or halo.

2. A compound according to claim 1 wherein R, $R^3$ and $R^4$ are hydrogen.

3. A compound according to claim 1 wherein $R^2$ is hydrogen or methyl.

4. A compound according to claim 1 wherein $R^1$ is 3,5-difluorophenyl, 3,4,5-trifluorophenyl, 3-trifluoromethylphenyl, 3-fluoro-5-trifluoromethylphenyl or 3-fluoro-4-methylphenyl.

5. A compound according to claim 1 wherein the compound is selected from the group consisting of 6-[1-(3,5-Difluoro-benzyl)-piperidin-4-ylamino]-pyridazine-3-carbonitrile, 6-[1-(3-Trifluoromethyl-benzyl)-piperidin-4-ylamino]-pyridazine-3-carbonitrile, 6-[1-(3-Fluoro-5-trifluoromethyl-benzyl)-piperidin-4-ylamino]-pyridazine-3-carbonitrile, 6-[1-(3,4,5-Trifluoro-benzyl)-piperidin-4-ylamino]-pyridazine-3-carbonitrile, and 6-[1-(3-Fluoro,4-methyl-benzyl)-piperidin-4-ylamino]-pyridazine-3-carbonitrile.

6. A pharmaceutical composition comprising a therapeutically effective amount of a compound as defined in claim 1.

7. A process of preparing a compound of Formula (I)

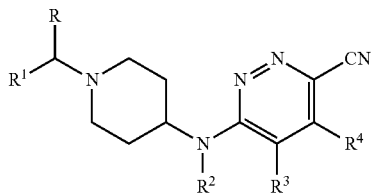

wherein R, $R^1$-$R^4$ are as defined in claim 1, comprising the step of (a) reacting an intermediate of Formula (II)

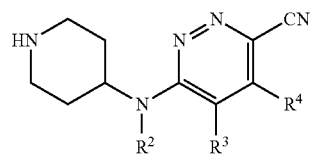

(II)

wherein $R^2$-$R^4$ are as defined in claim 1, with an intermediate of formula $R^1$—C(═O)—R, where R and $R^1$ are as defined in claim 1, in the presence of a reducing agent and an acid catalyst, in a reaction inert solvent; or (b) reacting an intermediate of Formula (VII)

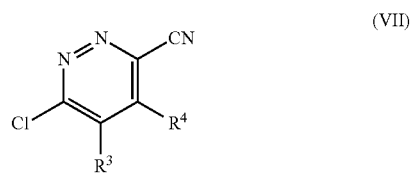

(VII)

wherein $R^3$ and $R^4$ are as defined in claim 1, with an intermediate of Formula (VIII)

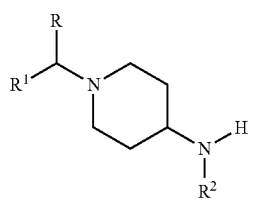

(VIII)

wherein R, $R^1$ and $R^2$ are as is as defined in claim 1, in the presence of a base in a reaction inert solvent.

\* \* \* \* \*